(12) United States Patent
Knyrim et al.

(10) Patent No.: US 8,585,983 B2
(45) Date of Patent: *Nov. 19, 2013

(54) HALOGEN AND HEAVY METAL-FREE COMPOSITION FOR A HUMIDITY INDICATING DEVICE AND HUMIDITY INDICATING DEVICE CONTAINING THE SAME

(75) Inventors: Johanna Knyrim, Munich (DE); Stefan Dick, Weichering (DE)

(73) Assignee: Sud-Chemie IP GmbH & Co. KG, Munich (DE)

( * ) Notice: Subject to any disclaimer, the term of this patent is extended or adjusted under 35 U.S.C. 154(b) by 288 days.

This patent is subject to a terminal disclaimer.

(21) Appl. No.: 13/165,932

(22) Filed: Jun. 22, 2011

(65) Prior Publication Data

US 2012/0329169 A1  Dec. 27, 2012

(51) Int. Cl.
*G01N 31/22* (2006.01)
(52) U.S. Cl.
USPC ........ 422/426; 252/408.1; 422/400; 422/401; 422/402; 422/425; 422/83; 436/163; 116/206
(58) Field of Classification Search
USPC ................... 422/426, 400, 401, 402, 425, 83; 436/163; 116/206; 252/408.1
See application file for complete search history.

(56) References Cited

U.S. PATENT DOCUMENTS

| | | |
|---|---|---|
| 2,214,354 A | 9/1940 | Snelling |
| 6,698,378 B1 | 3/2004 | Dick et al. |
| 6,877,457 B1 | 4/2005 | Dick et al. |
| 2003/0056710 A1 | 3/2003 | Radmacher et al. |
| 2005/0106735 A1 | 5/2005 | Song et al. |
| 2007/0157702 A1 | 7/2007 | Hamada |

FOREIGN PATENT DOCUMENTS

| | | |
|---|---|---|
| JP | 61154986 | 7/1986 |
| JP | 2007198828 | 8/2007 |
| JP | 2008111774 | 5/2008 |
| WO | 0109601 | 2/2001 |

OTHER PUBLICATIONS

Military Specification MIL-I-8835A.
"Handling, Packaging, and Use of Moisture/Reflow Sensitive Surface Mount Device," IPC/JEDEC J-STD-033B (Oct. 2005).

*Primary Examiner* — Monique Cole
(74) *Attorney, Agent, or Firm* — Scott R. Cox

(57) ABSTRACT

The disclosed invention is a composition for a humidity indicating device comprising (a) an organic pH indicator dye compound, (b) a Bronsted acid or base, and (c) a polyol having the general formula $HOCH_2$—$(CHOH)_n$—$CH_2OH$, wherein n can be 0, 1, 2, 3 or 4, wherein said components (a), (b), and (c) do not contain halogen and/or heavy metals.

Furthermore, the invention relates to a humidity indicator device comprising a sheet substrate and the composition for a humidity indicating device containing no heavy metals or halogen compounds, and to a process for preparing said humidity indicator device.

22 Claims, No Drawings

HALOGEN AND HEAVY METAL-FREE COMPOSITION FOR A HUMIDITY INDICATING DEVICE AND HUMIDITY INDICATING DEVICE CONTAINING THE SAME

TECHNICAL FIELD

The present invention relates to a composition for a humidity indicating device containing no heavy metals or halogen compounds, to a humidity indicating device comprising said composition and to a process for preparing said humidity indicating device.

BACKGROUND

When shipping or storing many types of materials, particularly electronic and semiconductor components, it is desirable to know whether those components have been exposed to a particular level of humidity of the surrounding atmosphere, which humidity could cause damage to those components. For instance, electronic components can be damaged by exposure to an atmosphere having a humidity exceeding a specific threshold level, even when the threshold level is low and the exposure is only for short period of time.

To address the need for the detection of humidity levels within shipping or storage containers, humidity indicators have been developed. There are generally two types of humidity indicators. One of these humidity indicators reversibly changes color upon exposure to particular humidity levels. Such reversible humidity indicators typically utilize cobalt chloride as the humidity indicator material impregnated on blotting paper. Military specification MIL-I-8835A describes the details of construction of such indicators and performance requirements. The indicators change color when exposed to predetermined levels of humidity and return to its original color when the humidity level drops below that predetermined level. Reversible humidity indicators are used to indicate the current condition of a desiccant and/or the current humidity level within the storage container.

The second type of humidity indicator is an irreversible humidity indicator. These indicators are designed to detect a predetermined level of humidity and provide a visual indication of whether components stored in the containers have been exposed to that predetermined level of humidity. The irreversible humidity indicator can therefore provide an indication when the humidity reaches the predetermined level even for short periods of time and even if the level of humidity drops below that predetermined level when the components are checked at a later time. Large changes in humidity levels sometimes occur where storage containers are used in relatively warm climates and when the moisture level in the air rises and falls dramatically depending upon the temperature of the surrounding air. Under these conditions, a reversible humidity indicator might fail to indicate the temporary presence of high humidity within a storage container even though such high humidity may be sufficient to cause damage to the components present in the storage container. Irreversible humidity indicator cards are described in patents U.S. Pat. Nos. 6,877,457 and 6,698,378, for example.

The advent of surface mount devices (SMDs) introduced a new class of quality and reliability concerns regarding package damage "cracks and delamination" from the solder reflow process and the effect of moisture within these areas. Moisture from atmospheric humidity enters permeable packaging materials by diffusion. Assembly processes used to solder SMD packages to printed circuit boards (PCBs) expose the entire package body to temperatures higher than 200° C. During solder reflow, the combination of rapid moisture expansion, materials mismatch, and material interface degradation can result in package cracking and/or delamination of critical interfaces within the package. The presence of moisture within these cracks and delaminations may have deleterious effects on the SMDs. To address this concern, the Electronics Industries Alliance/Joint Electron Device engineering Council (JEDEC) has developed a Joint Industry Standard directed to the "Handling, Packaging, and Use of Moisture/Reflow Sensitive Surface Mount Device, IPC/JEDEC J-STD-033B October 2005. This document describes the standardized levels of floor life exposure for moisture/reflow-sensitive SMD packages along with the handling, packing and shipping requirements necessary to avoid moisture/reflow-related failures.

In this standard, a humidity indicator card is defined as "[a] card on which a moisture-sensitive chemical is applied such that it will make a significant, perceptible change in color (hue), typically from blue (dry) to pink (wet) when the indicated relative humidity is exceeded." The standard further indicates that the humidity indicator card is normally packed inside a moisture-barrier bag, along with a desiccant and the SMDs, to aid in determining the level of moisture to which the moisture-sensitive devices have been subjected. Annex 1 of the standard describes a test to objectively assess the color change, and specifies minimum hue changes for humidity indicator cards in order to be suitable for SMD dry packing. The standard requires a humidity indicator card indicating humidity levels of relative humidity (RH) of 5% RH, 10% RH and 60% RH with an accuracy of +/−2% RH.

In the past, many humidity indicator cards for use in the electronic industry have used cobalt dichloride impregnated on blotting paper as the humidity indicating substance. These indicators change their color from blue (dry) to pink (wet) after exposure to certain levels of humidity. Cobalt dibromide has also been used a replacement to cobalt dichloride. However, humidity indicator cards based on cobalt dichloride and cobalt dibromide contain considerable amounts of heavy metals and halide anions.

Other humidity indicator card systems have been suggested based on copper chloride and synergistic salts (e.g. EP 1 200 819 A0, also published as WO 01/09601 A1). All formulations described in WO 01/09601 A1 contain copper chloride and up to 30 times the amount of copper chloride in synergistic salts, and thus exhibit a considerable amount of compounds containing halogen and heavy metals in the humidity indicator card.

In EP 1 293 773 A2, another humidity indicator card system has been suggested on the basis of certain pH indicator dyes, selected from the group of m-cresol purple, thymol blue, tropaeolin 00 and p-xylenol blue, and an excess of a zinc salt (e.g. zinc chloride) of at least 1:5, preferably 1:20 and most preferably 1:30. Humidity indicator cards based on this disclosure contain large amounts of anions as well as heavy metals due to the excess of zinc salts.

Yet another humidity indicator card system was suggested based in US 2005/0106735 A1 on pH indicator dyes, color enhancing additives (acids and bases) and hygroscopic salts. Hygroscopic salts like magnesium chloride and sodium chloride are needed to practice this invention, thus leading to a high amount of anions in the humidity indicator card. Neutral red is described herein in combination with sodium hydroxide and magnesium chloride to give indicator spots that change color from forest green (dry) to rusty brown when being moisturized.

A humidity indicator card based on formulations of a combination of pH indicators, such as neutral red, crystal violett, brilliant green, methyl violet, methyl orange and organic acid, such as acetic acid or citric acid, is suggested in US 2007/0157702 A1. It was found that this system shows no sharp color transition from a first color to a different second color when a specified humidity level is achieved. Furthermore, it was found that the system can not be adjusted to change color at different humidity levels.

In JP 2007-198828 A, a moisture indicator based on a bilayer constitution, layered sequentially with a pH indicator and a water-soluble salt containing layer is introduced. As pH indicators bromocresol green, methyl red, chlorophenol red, bromocresol purple, neutral red, phenol red, cresol red, alpha naphthol phthalein, curcumin, metacresol purple, ethylbis (2,4 dinitrophenyl)acetate, thymol blue, para-xylenol blue, phenolphthalein, alkali blue, alizarin yellow, phenol purple, phenol blue, and bromophenol blue are described. Further on the optional addition of glycerin as a moisturizer is mentioned.

An irreversible humidity indicator card system was suggested based on a deliquescent salt combined with a water-soluble dye and optionally wetting agents, penetrating agents, or spreading agents etc. in U.S. Pat. No. 2,214,354. These agents facilitate the absorption of water and diffusion of the used paper. The addition of dyes for an enhancement of the color change of a humidity indicator is known and described in the JP 61-154986.

Surprisingly, it has been found that the addition of certain color change enhancing agents to the impregnating solution to make a humidity indicator spot allows a formulation based on organic dyes without using heavy metals to maintain the nature of the color change and its accuracy known by heavy metal containing devices.

Only recently, the semiconductor and electronic industries have adopted specifications and standards for the restriction of amounts of certain elements present in their products. For example, these industries restrict the amounts of halogen (i.e. of compounds containing F, Cl, Br and/or I), phosphorous and certain heavy metals irrespective of the chemical nature of their presence. These restrictions apply to semiconductor and electronic products as well as to components and packaging materials, including humidity indicating devices.

Thus, there is a need of humidity indicating devices containing a reduced amount of halogens and free of heavy metals. However, accuracy, readability and reliability of conventional humidity indicating devices should not by deteriorated by the omission of heavy metals and halogen-containing compounds.

It is an object of the present invention to provide a composition for a humidity indicating device containing no halogen compounds and no heavy metals and having the same or improved accuracy, readability and reliability as compositions for conventional humidity indicating devices.

It is a second object of the present invention to provide a humidity indicating device containing only low amounts of halogen compounds and heavy metals and having the same or improved accuracy, readability and reliability as conventional humidity indicating devices.

It is a third object of the present invention to provide a process for preparing said humidity indicating device.

DESCRIPTION OF THE INVENTION

Surprisingly, it was found as a first aspect of the invention that said first object can be achieved by a composition for a humidity indicating device comprising (a) an organic pH indicator dye compound,
(b) a Bronsted acid or base,
(c) a polyol having the general formula $HOCH_2—(CHOH)_n—CH_2OH$,
wherein n can be 0, 1, 2, 3 or 4,
wherein said components (a), (b) and (c) do not contain halogen and/or heavy metals.

Thus, neither any of said components (a), (b) and (c) nor the composition as a whole contains an element of group 17 of the periodic system of elements which comprises F, Cl, Br, I and At.

Furthermore, neither any of said components (a), (b) and (c) nor the composition as a whole contains atoms or ions of a heavy metal such as cobalt, nickel, copper, zinc.

As a second aspect of the invention, it was surprisingly found that the second object of the invention can be achieved by a humidity indicating device comprising a sheet substrate and the composition according to the abovementioned first aspect of the invention in finely divided form in or on at least a part of a surface of said sheet substrate such that a colour impression caused by the composition can be observed on at least a part of the surface of the sheet substrate.

As a third aspect of the present invention, it was found that the third object of the invention can be achieved by a process comprising the steps of (i) providing a sheet substrate, and (ii) applying said composition according to the first aspect of the present invention onto at least a part of the surface of the sheet substrate.

In the following, the components of the composition for a humidity indicating device of the present invention will be explained in more detail.

(a) Organic pH Indicator Dye Compound

The organic pH indicator dye compound is an organic compound absorbing light from the spectrum visible to a human's eye such that the compound appears colored. The specific wavelength or range of wavelengths of the visible spectrum absorbed by the compound changes in reaction to a change in pH such the color impression caused by the compound changes. The compound is thus suitable to visually indicate a change in pH.

The specific pH range at which the color transition takes place depends on the molecular structure of the compound.

Commonly known organic pH indicator dye compounds are litmus, cyanidine, xylenol blue, neutral red, thymol blue, phenolphthalein, alizarin, alkaline blue, thymolphthalein each of which is suitable for being employed as component (a) in the composition for a humidity indicating device according to the present invention.

A triphenylmethan substructure is present in xylenol blue, thymol blue, phenolphthalein, alizarin, alkaline blue, thymolphthalein.

A phenazin substructure is present in neutral red. Neutral red is a preferred organic pH indicator dye compound due as it shows a pronounced color transition from blue to red which is similar to color transition observed in conventional humidity indicator cards containing cobalt chloride.

(b) Bronsted Acid or Base

A Bronsted acid is a compound that can donate a proton, and a Bronsted base is a compound that can receive a proton.

The Bronsted acid or base component of the composition for a humidity indicating device according to the present invention thus is capable of donating a proton to or of receiving a proton from the organic pH indicator dye compound (a) present in the composition in a dynamic equilibrium. Under the influence of the relative humidity of the surrounding atmosphere, the equilibrium is shifted more to the side of the protonated organic pH indicator dye compound (a) or more to the side of the unprotonated organic pH indicator dye compound (a) which results in a change of color of the organic pH indicator dye compound (a).

The pH generated by the Bronsted acid or base is influenced by the amount of said Bronsted acid or base and by its dissociation constant. Therefore, by varying the amount of Bronsted acid or base relative to the amount of a specific organic pH indicator dye compound (a), the specific relative humidity at which the color transition of the organic pH indicator dye compound (a) takes place can be influenced.

Alternatively or additionally, the pH generated can be influenced by selecting a specific Bronsted acid or base having a different dissociation constant. Thus, the relative humidity at which the color transition of a specific organic pH indicator dye compound (a) takes place can be also influenced by varying the specific Bronsted acid or base.

Alkali metal carbonates, alkali metal hydroxides, alkali metal acetates, acetic acid, citric acid, sulphuric acid, nitric acid can be mentioned as exemplary Bronsted acid or bases.

Preferably, the Bronsted acid or base is present in the composition for a humidity indicating device in an amount of 1 to 2,500 parts by weight, more preferably 30 to 200 parts by weight relative to 1 part by weight of said organic pH indicator dye compound.

(c) Polyol

The polyol (c) present in the composition for a humidity indicating device of the present invention increase the color impression of the organic pH indicator dye compound (a). Thus, visibility of the color transition of the organic pH indicator dye compound (a) is improved when relative humidity of the surrounding atmosphere changes.

The polyol has the general formula $HOCH_2—(CHOH)_n—CH_2OH$, wherein n is 0, 1, 2, 3 or 4. Ethylene glycol, glycerine, erythritol, xylitol, mannitol, sorbitol can be mentioned as exemplary compounds. A single polyol or combinations of two or more different polyols can be employed in the composition for a humidity indicating device of the present invention.

Xylitol and glycerine are preferred polyols as they give rise to a particularly advantageous improvement of the visibility of the color transition of the organic pH indicator dye compound (a).

Preferably, the polyol is present in the composition for a humidity indicating device in an amount of 0.02 to 50 parts by weight, more preferably 0.1 to 10 parts by weight relative to 1 part by weight of said Bronsted acid or base.

(d) Ascorbic Acid as Optional Component

The composition for a humidity indicating device of the present invention can comprise ascorbic acid as an additional component. When ascorbic acid is present in the composition for a humidity indicating device, the amount is in essence limited only by its solubility in the solvent (e), or, if the solvent (e) is omitted, in any of the components (b) and/or (c) having the suitability to dissolve the other components of the composition. Preferably, ascorbic acid is present in an amount of 1 to 3 parts by weight relative to said Bronsted acid or base.

(e) Solvent as an Optional Component

In order to apply the composition according to the first aspect of the invention to the sheet substrate and in order to finely distribute the composition in or on at least a part of the surface of the sheet substrate, the components (a), (b) and (c) can be dissolved in a solvent. If the polyol (c) and/or the Bronsted acid or base (b) have properties suitable for dissolving the components of the composition and are present in an amount suitable for forming a solution of the components of the composition, the solvent (e) can be omitted. Thus, the solvent (e) is an optional component of the composition for a humidity indicating device.

The solvent is not particularly limited and is appropriately selected from compounds which (i) have properties suitable for dissolving the compounds of the composition and (ii) can be conveniently removed from the composition without resulting in a deterioration of the components of the composition, for instance due to thermally induced decomposition of one or more of said components if the solvent is removed by evaporation at elevated temperature. The solvent can be selected from water, methanol, ethanol, acetone and combinations thereof.

As water is not toxic or flammable and hence does not require venting of the production site, it is a preferred solvent of the composition for a humidity indicating device according to the present invention.

A mixture of water and ethanol can be used as the solvent when water alone is not suitable for dissolving the components (a), (b) and (c).

The amount of solvent present in the composition for a humidity indicating device is suitably selected in order to accomplish complete dissolution of the components of the composition for a humidity indicating device. An excess of solvent should be avoided as otherwise the colour impression of the composition after removal of the solvent on the humidity indicating device is not sufficiently strong in order to result in a clearly visible spot changing its color when relative humidity of the surrounding atmosphere changes. Preferably, the solvent is present in the composition for a humidity indicating device in an amount of 20 to 70,000 parts by weight, more preferably 1000 to 35,000 parts by weight, relative to 1 part by weight of said organic pH indicator dye compound.

Composition for a Humidity Indicating Device

As mentioned hereinabove, the composition for a humidity indicating device according to the present invention does not contain halogen and heavy metals. This means that no compounds containing halogens and heavy metals are deliberately added and/or have any functional purpose. However, the presence of detectable traces of salts and/or compounds of halogen and/or heavy metals can not be completely excluded due to the ubiquitous occurrence of such salts and/or compounds.

In the following, especially preferred combinations of components (a), (b) and (c) are described.

The combination of Neutral red as the organic pH indicator dye compound (a), sulphuric acid as the Bronsted acid or base (b), glycerine as the polyol (c) and water as the solvent (e) is preferred as it can be applied to a sheet substrate by printing or spotting manually or by using an appropriate apparatus and, after having been applied to a sheet substrate, gives rise to a clear color change from blue in a dry atmosphere (a relative humidity of 0%) to purple or pink in an atmosphere having a relative humidity of 60%.

A particularly preferred combination comprises Neutral red as the organic pH indicator dye compound (a), sulphuric acid as the Bronsted acid or base (b), glycerine as the polyol (c), ascorbic acid (d) and water as the solvent (e). It has surprisingly been found that the presence of ascorbic acid gives rise to a brilliant blue color of the composition for a humidity indicating device in a dry atmosphere (a relative humidity of 0%) after the solvent was removed. As result, the color change to purple or pink in an atmosphere having an elevated relative humidity, such as 60%, is more clearly visible.

The composition for a humidity indicating device is prepared by mixing components (a), (b), (c) and optionally ascorbic acid (d), optionally in solvent (e), in amounts as described hereinabove by using any means suitable for mixing a composition having a viscosity that is essentially the same as the viscosity of said solvent or, if the solvent (e) is omitted, as the viscosity of the liquid components (b) and/or (c). The sequence of mixing components (a), (b), (c) and the optional components ascorbic acid and solvent is not particularly restricted.

Humidity Indicating Device

The humidity indicating device according to the present invention comprises a sheet substrate and the above-described composition in finely divided form.

The composition for a humidity indicating device is arranged in finely divided form in or on at least a part of the surface of said sheet substrate. Fine division of the composition can for instance be achieved by applying the composition to the substrate in the form of a solution in solvent (e) and subsequently evaporating the solvent. The expression "in or on at least a part of the surface" means that the composition can be present on the surface of the substrate or can be taken up into the substrate (for instance as a solution in said solvent (e)) such that the composition is present in regions of the substrate that are adjacent to the surface. Thus, the colour impression caused by the composition is visible on the surface of the substrate.

Preferably, different compositions for a humidity indicating device showing a change of colour at different levels of relative humidity can be provided on different parts of the surface of the sheet material in order to render the humidity indicating device suitable for indicating several levels of relative humidity of the surrounding atmosphere. For instance, three different humidity indicating compositions can be provided in different spots on a surface of the sheet material.

The sheet substrate may be formed from a material having fine open voids in which a liquid applied to the surface of the material can be accommodated. For instance, the voids can exhibit a capillary effect such that a liquid applied to a surface of the material is taken up by the voids. A material having fine open voids can be a material containing fibres. Said fibres can be formed of natural or synthetic materials such as natural or synthetic polymers, natural or synthetic minerals, glass etc. or mixtures thereof. As an exemplary natural polymer, cellulose can be mentioned.

Thus, the sheet material can be a woven or non-woven material containing fibres. For example, the sheet substrate can be formed from conventional blotting paper. In one embodiment, white blotting paper made from fibrous cellulosic material with a minimal basis weight of 200 g/m$^2$ is used.

In a material having fine open voids a solution of the composition for a humidity indicating device as described hereinabove can be accommodated, for instance by applying a composition comprising components (a), (b) and (c) and a solvent (e) to said material and allowing the solvent to evaporate. After the solvent has been removed, the components (a), (b) and (c) of the composition remain in a finely divided form.

The sheet substrate can contain additives common in the manufacture of paper and/or plastic sheets such as barium sulphate, titanium dioxide, calcium carbonate, aluminium oxide, zinc oxide and basic lead carbonate. Said compounds are commonly used in the manufacturing process of such sheet substrates as pigments and/or fillers etc. Furthermore, traces of chloride can be present in a sheet substrate such as paper which result from the manufacturing process. Thus, although the composition for a humidity indicating device of the present invention does not contain halogen compounds and heavy metals (except for traces inevitable in view of the ubiquitous occurrence of halogens, heavy metals and their salts and compounds as indicated hereinabove), the humidity indicator device can contain low amounts of halogen compounds and/or heavy metals. Said halogen compounds and/or heavy metals have no function in the composition for a humidity indicating device and in the humidity indicating device of the present invention.

The sheet substrate and the humidity indicating device can have any conceivable geometric shape. Usually, the shape of the sheet substrate is circular or regular-polygonal (such as rectangular, for instance). A specific geometric shape can be imparted by cutting using a blade or by die cutting, for instance.

In use, the humidity indicating device is placed in a shipping container or storage container for equipment, e.g. electronic equipment or electronic components, such as integrated circuits. Humidity present in the air within the container will be adsorbed by the dry composition on the sheet substrate to indicate the specified humidity level.

Once the composition for a humidity indicating device has been dried on a sheet substrate and is placed in an environment having the specified humidity level, the color of the appropriate color spot will change from a certain color to another, thereby indicating the existence of that particular humidity level and the actions required to protect the electronic equipment as provided in the written instructions.

Process for Preparing a Humidity Indicating Device

The process for preparing a humidity indicating device according to the present invention comprises the steps of
(i) providing a sheet substrate as described hereinabove,
(ii) applying the composition for a humidity indicating device as described hereinabove onto at least a part of a surface of the sheet substrate, and
(iii) if a solvent is present in the composition, removing the solvent (e) from the composition for a humidity indicating device.

When the sheet substrate is formed of a material having fine open voids, the composition for a humidity indicating device as described hereinabove can be accommodated in the voids, for instance by capillary action. As a result, the composition is arranged in the surface of the sheet substrate in finely divided form.

Optionally, step (ii) is repeated using a different composition for a humidity indicating device, when it is intended to provide several areas on the sheet substrate each of which areas shows a color change at different conditions of relative humidity of the surrounding atmosphere.

The step of applying the composition for a humidity indicating device onto a surface of the sheet substrate can be carried out by any operation suitable for applying a low-viscous solution to a sheet substrate such as printing or spotting.

As mentioned hereinabove, a solvent (e) can be added to the composition in order to form a solution of the composition. If a solvent is present, the solvent is removed from the composition after the composition has been applied to the surface of the sheet substrate. Removing the solvent can be carried out by allowing the solvent to evaporate for instance.

Allowing the solvent to evaporate can be effected at room temperature or at an elevated temperature until the indicator device shows the color indicating a dry state. The specific temperature can be suitably selected in order to achieve that the period of time required for evaporating the solvent is acceptably short. A too high temperature can result in grey or black discoloration of the spots of the composition for a humidity indicating device applied to the surface of the sheet substrate and should hence be avoided.

EXAMPLES

Example 1—Comparative

Humidity indicating device were prepared using the neutral red/sulphuric acid formulations disclosed in Table 1. These solutions were hand-spotted on commercial white blotting paper (FiberMark, Brattleboro, Vt.) with a basis weight of 300 g/m² and dried at 80° C. for 15 minutes. For each spot, 50 μl of solution was used and the device weight was 1.00 g.

TABLE 1

| | | | | |
|---|---|---|---|---|
| 70% Ethanol (ml) | 100 | 100 | 100 | 100 |
| Neutral red (g) | 0.075 | 0.075 | 0.075 | 0.075 |
| Sulphuric acid conc (ml) | 0.8 | 1.6 | 2.4 | 3.6 |
| Color @ 0% r.h. | Pink | Purple | Blue | Grey-Green |
| Color @ 20% r.h. | Pink | Purple | Blue | Grey-Green |
| Color @ 40% r.h. | Pink | Purple | Blue | Grey-Green |
| Color @ 60% r.h. | Pink | Purple | Blue-Purple | Grey-Blue |

Example 2

Humidity indicating device using xylitol as well as ascorbic acid were prepared using the neutral red/acid formulations disclosed in Tables 2-4. These solutions were hand-spotted on commercial white blotting paper (FiberMark, Brattleboro, Vt.) with a basis weight of 300 g/m² and dried at 80° C. for 15 minutes. For each spot, 50 it of solution was used and the device weight was 1.00 g.

TABLE 2

| | | | |
|---|---|---|---|
| 70% Ethanol (ml) | 100 | 100 | 100 |
| Neutral red (g) | 0.08 | 0.08 | 0.08 |
| Sulphuric acid conc (ml) | 2 | 2 | 2 |
| Ascorbic acid (g) | 0 | 1 | 2 |
| Xylitol (g) | 0 | 0 | 0 |
| Color @ 0% r.h. | Grey | Blue | Blue |
| Color @ 30% r.h. | Grey-Purple | Blue | Blue |
| Color @ 50% r.h. | Purple | Purple | Blue |

TABLE 3

| | | | |
|---|---|---|---|
| Ethanol (ml) | 100 | 100 | 100 |
| Neutral red (g) | 0.08 | 0.08 | 0.08 |
| Sulphuric acid conc (ml) | 2 | 2 | 2 |
| Ascorbic acid (g) | 0 | 1 | 2 |
| Xylitol (g) | 1 | 1 | 1 |
| Color @ 0% r.h. | Blue | Blue | Blue |
| Color @ 30% r.h. | Pink | Blue-Purple | Blue |
| Color @ 50% r.h. | Pink | Pink | Purple |

TABLE 4

| | | | |
|---|---|---|---|
| Ethanol (ml) | 100 | 100 | 100 |
| Neutral red (g) | 0.08 | 0.08 | 0.08 |
| Sulphuric acid conc (ml) | 2 | 2 | 2 |
| Ascorbic acid (g) | 0 | 1 | 2 |
| Xylitol (g) | 2 | 2 | 2 |
| Color @ 0% r.h. | Blue-Purple | Blue | Blue |
| Color @ 30% r.h. | Pink | Purple | Purple |
| Color @ 50% r.h. | Pink | Pink | Pink |

Surprisingly, the addition of ascorbic acid leads to brilliant blue spots and prevents discoloration to grey.

Example 3

Acidic Neutral red formulations using the following polyols were prepared:
CCE1: Glycerine
CCE2: Ethylene glycol
CCE3: Xylitol
CCE4: Sorbitol
CCE5: Erythritol These solutions were hand-spotted on commercial white blotting paper (FiberMark, Brattleboro, Vt.) with a basis weight of 300 g/m² and dried at 80° C. for 15 minutes. For each spot, 15 μl of solution was used to create 12 mm diameter spots.

TABLE 5

| Type of polyol | None | CCE 1 | CCE 2 | CCE 3 | CCE 4 | CCE 5 |
|---|---|---|---|---|---|---|
| 70% Ethanol (ml) | 100 | 100 | 100 | 100 | 100 | 100 |
| Sulphuric acid conc (ml) | 2 | 2 | 2 | 2 | 2 | 2 |
| Ascorbic acid (g) | 10 | 10 | 10 | 10 | 10 | 10 |
| Neutral red (g) | 0.05 | 0.05 | 0.05 | 0.05 | 0.05 | 0.05 |
| Amount of polyol (g) | 0 | 19 | 19 | 19 | 19 | 19 |
| Color @ 0% r.h. | Blue | Blue | Blue | Blue | Blue | Blue |
| Color @ 20% r.h. | Blue | Purple | Purple-pink | Purple | Purple | Purple |
| Color @ 40% r.h. | Blue | Pink | Pink | Pink | Pink | Pink |

TABLE 6

| Type of polyol | None | CCE 1 | CCE 2 | CCE 3 | CCE 4 | CCE 5 |
|---|---|---|---|---|---|---|
| 70% Ethanol (ml) | 100 | 100 | 100 | 100 | 100 | 100 |
| Sulphuric acid conc (ml) | 2 | 2 | 2 | 2 | 2 | 2 |
| Ascorbic acid (g) | 10 | 10 | 10 | 10 | 10 | 10 |
| Neutral red (g) | 0.05 | 0.05 | 0.05 | 0.05 | 0.05 | 0.05 |
| Amount of polyol (g) | 0 | 32 | 32 | 32 | 32 | 32 |
| Color @ 0% r.h. | Blue | Blue | Blue | Blue | Blue | Blue |
| Color @ 20% r.h. | Blue | Purple-Pink | Pink | Purple-Pink | Purple | Purple |
| Color @ 40% r.h. | Blue | Pink | Pink | Pink | Pink | Pink |

These solutions were hand-spotted on commercial white blotting paper (FiberMark, Brattleboro, Vt.) with a basis weight of 300 g/m² and dried at 80° C. for 15 minutes. For each spot, 50 μl of solution was used and the device weight was 1.00 g.

The principles, preferred embodiments and modes of operation in the present invention have been described in the aforementioned specification. The invention, which is intended to be protected herein, is not to be construed as limited to the particular structures or embodiments disclosed, as these are to be regarded as illustrative rather than restrictive. Variations and changes may be made by those skilled in the art without departing from the invention.

The invention claimed is:

1. Composition for a humidity indicating device comprising
    (a) an organic pH indicator dye compound,
    (b) a Bronsted acid or base, and
    (c) a polyol having the general formula
        $HOCH_2$—$(CHOH)_n$—$CH_2OH$, wherein n is selected from the group consisting of 0, 1, 2, 3 and 4, wherein said components (a), (b) and (c) do not contain a halogen and heavy metals.

2. Composition according to claim 1, wherein said organic pH indicator dye compound is selected from the group consisting of phenazine dyes, triphenylmethane dyes and combinations thereof.

3. Composition according to claim 1, wherein said organic pH indicator dye compound is selected from the group consisting of litmus, cyanidine, xylenol blue, neutral red, thymol blue, phenolphthalein, alizarin, alkaline blue, thymolphthalein and combinations thereof.

4. Composition according to claim 1, wherein said Bronsted acid or base is selected from the group consisting of alkali metal carbonates, alkali metal hydroxides, alkali metal acetates, acetic acid, citric acid, sulphuric acid, nitric acid and combinations thereof.

5. Composition according to claim 1, wherein said polyol is selected from the group consisting of ethylene glycol, glycerine, erythritol, xylitol, mannitol, sorbitol and combinations thereof.

6. Composition according to claim 1 wherein said organic pH indicator dye compound comprises Neutral red;
    said Bronsted acid or base comprises sulphuric acid; and
    said polyol is selected from the group consisting of glycerine, xylitol and combinations thereof.

7. Composition according to claim 1 wherein said Bronsted acid or base is present in an amount of 1 to 2500 parts by weight relative to 1 part by weight of said organic pH indicator dye compound, and
    said polyol is present in an amount of 0.02 to 50 parts by weight relative to 1 part by weight of said Bronsted acid or base.

8. Composition according to claim 1, further comprising (d) ascorbic acid.

9. Composition according to claim 8, wherein the ascorbic acid is present in an amount of 1 to 3 parts by weight relative to 1 part by weight of said Bronsted acid or base.

10. Composition according to claim 1, further comprising (d) a solvent.

11. Composition according to claim 10, wherein said solvent is selected from the group consisting of water, methanol, ethanol, acetone and combinations thereof.

12. Composition according to claim 10, wherein said solvent is present in an amount of 20 to 70,000 parts by weight relative to 1 part by weight of organic pH indicator dye compound.

13. Humidity indicating device comprising
    (i) a sheet substrate,
    (ii) the composition as defined in claim 1 in or on at least a part of the surface of the sheet substrate.

14. Humidity indicating device according to claim 13, wherein said sheet substrate is selected from the group consisting of blotting paper, woven materials, non-woven materials and combinations thereof.

15. Humidity indicating device according to claim 14, wherein said sheet substrate comprises white blotting paper made from a fibrous cellulosic material.

16. A process for preparing a humidity indicating device comprising the steps of
    (i) providing a sheet substrate,
    (ii) applying the composition of claim 1 onto at least a part of the surface of the sheet substrate.

17. A process for preparing a humidity indicating device comprising the steps of
    (i) providing a sheet substrate,
    (ii) applying the composition of claim 10 onto at least a part of the surface of the sheet substrate, and
    (iii) allowing the solvent (d) to evaporate.

18. Composition according to claim 8, further comprising (e) a solvent.

19. Composition according to claim 18, wherein the ascorbic acid is present in an amount of 1 to 3 parts by weight relative to 1 part by weight of said Bronsted acid or base.

20. Composition according to claim 18, wherein said solvent is selected from the group consisting of water, methanol, ethanol, acetone and combinations thereof.

21. Composition according to claim 18, wherein said solvent is present in an amount of 20 to 70,000 parts by weight relative to 1 part by weight of organic pH indicator dye compound.

22. A process for preparing a humidity indicating device comprising the steps of
    (i) providing a sheet substrate,
    (ii) applying the composition of as defined in claim 18 onto at least a part of the surface of the sheet substrate and
    (iii) allowing the solvent (e) of the humidity indicating composition to evaporate.

* * * * *